(12) United States Patent
Kumar et al.

(10) Patent No.: US 7,084,301 B2
(45) Date of Patent: Aug. 1, 2006

(54) TAMSULOSIN DERIVATIVE

(75) Inventors: Yatendra Kumar, Haryana (IN); Ram Chander Aryan, Delhi (IN); Radhakrishnan Gowri Shankar, Haryana (IN); Kumar Hari Bhushan, Bihar (IN); Anita Chugh, Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 11/016,264

(22) Filed: Dec. 17, 2004

(65) Prior Publication Data

US 2005/0154231 A1  Jul. 14, 2005

Related U.S. Application Data

(62) Division of application No. 10/341,867, filed on Jan. 14, 2003, now Pat. No. 6,894,188.

(51) Int. Cl.
*A61K 31/18* (2006.01)
*C07C 303/40* (2006.01)

(52) U.S. Cl. .................................. 564/86; 514/603

(58) Field of Classification Search ............ 564/86; 514/603
See application file for complete search history.

(56) References Cited

U.S. PATENT DOCUMENTS

| 4,703,063 A | 10/1987 | Imai et al. ............ 514/603 |
| 4,731,478 A | 3/1988 | Niigata et al. ............ 564/86 |
| 5,391,825 A | 2/1995 | Niigata et al. ............ 564/88 |

FOREIGN PATENT DOCUMENTS

CA   1282077   3/1991

OTHER PUBLICATIONS

Taguchi et al., "Effects of Tamsulosin Metabolites in Alpha-1 Adrenoceptor Subtypes", *The Journal of Pharmacology and Experimental Therapeutics*, 280(1):1-5 (1997).
Soeishi et al., "Metabolism of tamsulosin in rat and dog", *Xenobiotica*, 26(3):355-365 (1996).
Soeishi et al., "Absorption, metabolism and excretion of tamsulosin hydrochloride in man", *Xenobiotica*, 26(6):637-645 (1996).
Wheeler et al., "The Synthesis of the $^{14}$C and [2]H-Isotopomers of (R)-N-[2-(2'-Ethoxyphenoxy)-Ethyl]-N-2-[3-(4'-Methoxy-3'-Sulfonamido)-Phenyl]-Propylamine Hydrochloride, an $\alpha_1$-Adrenoreceptor Antagonist[1]", *Journal of Labelled Compounds and Radiopharmaceuticals*, 27(2):171-180 (1989).
Vatz, "Alpha$_1$-Adrenergic Blockers: Do They Have a Place in the Prophylaxis of Migraine?", *Headache*, 37:107-108 (1997).
Kuo et al., "Design, Synthesis, and Structure-Activity Relationships of Phthalimide-Phenylpiperazines: A Novel Series of Potent and Selective $\alpha_{1a}$-Adrenergic Receptor Antagonists", *Journal of Medicinal Chemistry*, 43:2183-2195 (2000).
Lee et al., "Cardiovascular Activity of A-74283, a 5-Hydroxytryptamine$_{1a}$ Agent, in the Spontaneously Hypertensive Rat", *Pharmacology*, 56(1):17-29 (1998).
Schiffrin et al., "Platelet binding sites and plasma concetration of atrial natriuretic peptide in patients with essential hypertension", *Journal of Hypertension*, 6(7):565-572 (1988).
Dando et al., "Modulation of the vagal bradycardia evoked by stimulation of upper airway receptors by central 5-HT$_1$ receptors in anaesthetized rabbits", *British Journal of Pharmacology*, 125:409-417 (1998).
Phillips et al., "The effects of the novel anxiolytic drug lesopitron, a full and selective 5-HT$_{1a}$ receptor agonist, on pupil diameter and oral temperature in man: comparison with buspirone", *Journal of Psychopharmacology*, 13(4):391-397 (1999).
Testa et al., "Effect of Several 5-Hydroxytryptamine$_{1A}$ Receptor Ligands on the Micturition Reflex in Rats: Comparison with WAY 100635[1]", *The Journal of Pharmacology and Experimental Therapeutics*, 290(3):1258-1269 (1999).
Jose et al., "Role of dopamine receptors in the kidney in the regulation of blood pressure", *Current Opinion in Nephrology and Hypertension*, 11(1):87-92 (2002).
Mühlbauer et al., "Dopamine D$_3$ receptors in the rat kidney: role in physiology and pathophysiology" *Acta Physiologica Scandinavica*, 168(1):219-223 (2000).
Velasco et al., "Dopaminergic receptors: a new antihypertensive mechanism", *Journal of Hypertension*, 20(S3):S55-S58 (2002).

(Continued)

Primary Examiner—Peter O'Sullivan
(74) *Attorney, Agent, or Firm*—Jayadeep R. Deshmukh, Esq.; George E. Heibel, Esq.; William D. Hare, Esq.

(57) ABSTRACT

The optically active compound, R (−)-5-[2-[[2-(2-ethoxyphenoxy)ethyl]amino]propyl]-2-hydroxybenzenesulfonamide in good optical purity, a metabolite of the $\alpha_1$-adrenergic blocking agent tamsulosin, and methods for the preparation thereof. Pharmaceutical compositions including the optically active compound and methods of treatment comprising administration of an effective $\alpha_1$-adrenergic antagonistic amount of such compositions to mammals.

4 Claims, 1 Drawing Sheet

OTHER PUBLICATIONS

Amenta et al., "The Dopaminergic System in Hypertension", *Clinical and Experimental Hypertension*, 23(1&2):15-24 (2001).

Keffel et al., "$\alpha_1$-Adrenoceptor Subtypes Differentially Couple to Growth Promotion and Inhibition in Chinese Hamster Ovary Cells", *Biochemical and Biophysical Research Communications*, 272:906-911 (2000).

Michel et al., "Identification of a single $\alpha_1$-adrenoceptor corresponding to the $\alpha_{1A}$-subtype in rat submaxillary gland", *British Journal of Pharmacology*, 98:883-889 (1989).

Cheng & Prusoff, "Relationship Between the Inhibition Constant ($K_1$) and the Concentration of Inhibitor Which Causes 50 Per Cent Inhibition ($I_{50}$) of an Enzymatic Reaction", *Biochemical Pharmacology*, 22:3099-3108 (1973).

Martin et al., "Classification Review. Receptors for 5-Hydroxytryptamine: Current Perspectives on Classification and Nomenclature", *Neuropharmacology*, 33(3/4):261-273 (1994).

Sokoloff et al., "Molecular cloning and characterization of a novel dopamine receptor ($D_3$) as a target for neuroleptics", *Nature*, 347:146-151 (1990).

TAMSULOSIN DERIVATIVE

RELATED APPLICATIONS

This application is a divisional application of prior U.S. patent application Ser. No. 10/341,867, filed on 14 Jan. 2003, now U.S. Pat. No. 6,894,188 the disclosure of which is hereby incorporated by reference in its entirety. Both the instant application and the parent U.S. application claim the foreign priority of Indian Patent Application Serial No. 503/DEL/2002, filed 30 Apr. 2002, the disclosure of which is hereby incorporated by reference in its entirety.

FIELD OF THE INVENTION

The present invention relates to R (−)-5-[2-[[2-(2-ethoxyphenoxy)ethyl]amino]propyl]-2-hydroxybenzenesulfonamide, a metabolite of the $\alpha_1$-adrenergic blocking agent tamsulosin. The invention concerns methods for the preparation of the optically active compound, novel pharmaceutical compositions comprising the same and methods of treatment comprising administration of such compositions.

BACKGROUND

Several sulfamoyl substituted phenethylamine derivatives having strong α-adrenergic blocking activity are disclosed in U.S. Pat. No. 4,703,063. U.S. Pat. No. 4,731,478 discloses the (−) isomer of 5-[2-[2-(2-ethoxyphenoxy)ethylamino]-2-methylethyl]-2-methoxybenzene sulfonamide, that is, tamsulosin, having the following formula:

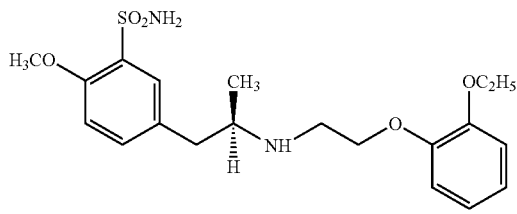

Tamsulosin is used in the treatment of benign prostatic hyperplasia (BPH), a condition characterized by enlargement of prostatic tissue, which results in obstruction of proximal urethra.

Tamsulosin primarily metabolizes to mainly five metabolites, one of which $M_4$ of Formula I has been found to be almost equipotent to tamsulosin with respect to $\alpha_1$ adrenoreceptor binding (Taguchi et al., *J. Pharmacol. Exp. Ther.*, 1997, 280 (1), 1–5). The authors specify that $M_4$ was used in its racemic form. The optically-active single enantiomer of this metabolite could not be obtained viz., *Xenobiotica*, (1996), 26(3), 355–365; and *Xenobiotica*, (1996), 26(6), 637–645.

Enantiomers are structurally identical compounds, which differ only in that one isomer is a mirror image of the other and the mirror images cannot be superimposed. This phenomenon is known as chirality. Most biological molecules exist as enantiomers and exhibit chirality. Although structurally identical, enantiomers can have profoundly different effects in biological systems: one enantiomer may have a specific biological activity while the other enantiomer has no biological activity at all, or may have an entirely different form of biological activity.

Therefore, there is a need to develop a method for the preparation of optically active compound of Formula I in order to explore the potential of the compound as $\alpha_1$-adrenoceptor antagonist. Our attempts to obtain the desired compound directly from tamsulosin by selective O-demethylation of tamsulosin have been unsuccessful.

SUMMARY

It has now been found that the compound of Formula I may be prepared by a simple and convenient process using convenient starting materials. The compound can be prepared in an isolated state. Accordingly, the present invention provides synthetic compound of Formula I, which has the chemical name R (−)-5-[2-[[2-(2-ethoxyphenoxy)ethyl]amino]propyl]-2-hydroxybenzene-sulfonamide and, pharmaceutically acceptable acid addition salts thereof. The compounds of the present invention have strong $\alpha_1$-adrenergic blocking activity.

Further, methods are provided for preparing the compound of Formula I, and pharmaceutically acceptable acid addition salts thereof, which comprise condensing a chiral primary amine of Formula II or a salt thereof, with an aldehyde of

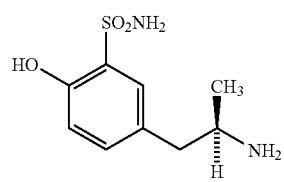

Formula III in the presence of sodium cyanoborohydride, followed by isolation of the enantiomer of Formula I as the free base, or a pharmaceutically acceptable acid addition salt thereof.

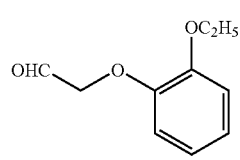

Formula I

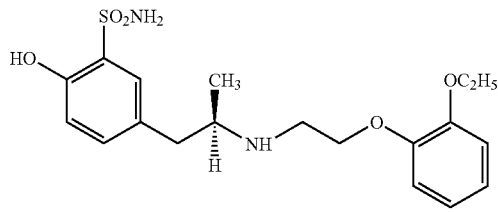

The process gives the compound of Formula I in an isolated state for the first time. The compound of Formula I can be isolated in optical purity of for example at least about 51% with respect to the other corresponding enantiomer, or for example in optical purity of at least about 60%, or at least about 75%, or at least about 80%, or at least about 90%. In some particular embodiments, the compound of Formula I can be prepared in an isolated state corresponding to at least about 95% optical purity, or at least about 98%, or at least 99%, or at least about 99.5% optical purity with respect to the other corresponding enantiomer. The process is advantageous in that the conversion of compound of Formula II to compound of Formula I is achieved in a single step as the imine formation and its reduction to amine proceed simultaneously. Also, no protection/deprotection of the aldehyde of Formula III is required.

Chiral phenethylamine compounds of formula II are not previously known, and are key intermediates of the process of the present invention.

The present invention provides a method for the preparation of a chiral primary amine intermediate of Formula II, and pharmaceutically acceptable acid addition salts thereof, which comprises reacting a chiral phenethylamine compound of Formula IV or a salt thereof, with

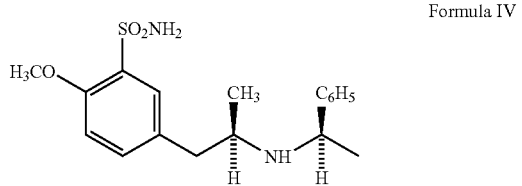

Formula IV a Lewis acid, and hydrogenating the obtained 2-hydroxybenzenesulfonamide compound of

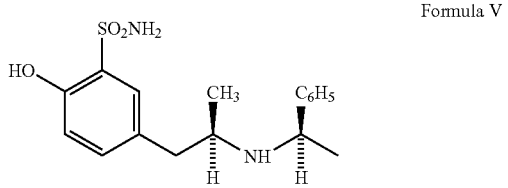

Formula V

Formula V or a salt thereof, to get an intermediate of Formula II, which may then be converted to a salt if desired.

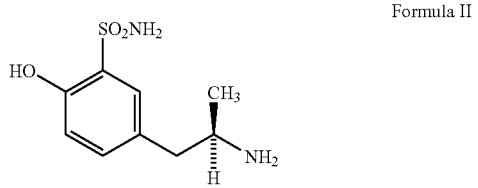

Formula II

The process gives a chiral amine of Formula II in good optical purity and no racemization or inversion is observed.

Pharmaceutical compositions of compound of Formula I and pharmaceutically acceptable acid addition salts thereof, in admixture with a solid or liquid pharmaceutical diluent or carrier can be employed for methods of producing $\alpha_1$-adrenergic antagonistic action in mammals.

DETAILED DESCRIPTION

Figure 1A:
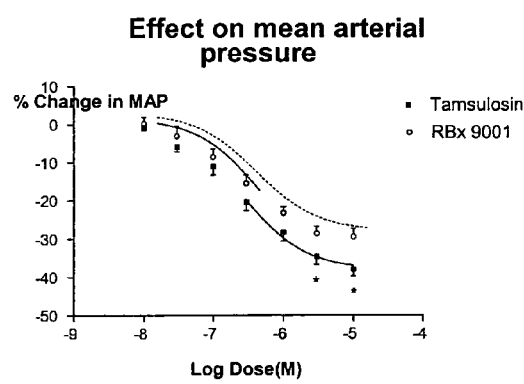
FIG. 1a is a graph of the effect of the log of the concentration of tamsulosin and of the compound of Formula I on the mean arterial blood pressure in normotensive rats, as expressed in percentage change in mean arterial pressure (MAP).

Compounds of Formula I can form pharmaceutically acceptable acid addition salts with inorganic or organic acid. Examples of such inorganic acids are hydrochloric, hydrobromic, hydroiodic, sulfuric, sulfamic, phosphoric and nitric acid, while examples of such organic acids are maleic, fumaric, benzoic, ascorbic, succinic, oxalic, methane sulfonic, ethane disulfonic, formic, acetic, propionic, tartaric, salicyclic, citric, gluconic, aspartic, stearic, palmitic, glycolic, p-aminobenzoic, glutamic, and benzenesulfonic acid. A particular example is the hydrochloride salt.

Intermediate compounds of Formulas II, IV and V may also be prepared or used in the form of acid addition salts, which may be the same or different from each other, and from the salt of Formula I. Any suitable inorganic or organic acid commonly used in synthetic chemistry may be used for salt formation. Examples of such acids include the acids given above for the compound of Formula I. A particular example is the hydrochloride salt.

The compound of Formula I can be prepared having at least 90% by weight of the R(−) isomer, and 10% or less of the S(+) isomer. For example, the compound of Formula I can be prepared having at least 95% by weight of the R(−) isomer, or at least 98% by weight of the R(−) isomer, or at least 99% by weight of the R(−) isomer. In some embodiments, the compound of Formula I can be prepared having at least 99.5% by weight of the R(−) isomer, and 0.5% or less of the S(+) isomer. The same and higher optical purities can be achieved for the compound of Formula II.

The compound of Formula I of this invention and its salts may exist in unsolvated or solvated form with pharmaceutically acceptable solvents such as water, ethanol, isopropanol and the like.

The chiral primary amine intermediate of Formula II is condensed with aldehyde of Formula III in the presence of sodium cyanoborohydride. The reaction may be carried out in a protic solvent such as methanol, ethanol, isopropanol, and mixtures thereof. Methanol is a particular example. Reaction can be performed at ambient temperature.

The starting aldehyde of Formula III may be prepared by the process of reference Example 1 of Canadian patent CA 1,282,077.

The starting chiral compound of Formula IV, used for the preparation of the key intermediate of Formula II, can be prepared easily by methods known in the art, such as J. Labelled Compd. Radiopharm., (1989), 27(2), 171–180, or by the preparation of (3-sulfonamido-4-methoxyphenyl)-2-propanone and conversion into the compound of Formula IV. The compound of Formula IV for use in preparation of the compound of Formula II can be prepared having at least 90% by weight of the R,R(+) isomer, and 10% or less of the R,S isomer. For example, the compound of Formula IV can be prepared having at least 95% by weight of the R,R(+) isomer, or at least 98% by weight of the R,R(+) isomer, or at least 99% by weight of the R,R(+) isomer. In some embodiments, the compound of Formula IV can be prepared having at least 99.5% by weight of the R,R(+) isomer, and 0.5% or less of the R,S isomer.

The compound of Formula IV is subjected to O-demethylation reaction in the presence of a Lewis acid. Suitable Lewis acids include halides of aluminum, boron, zinc, iron, tin, bismuth, antimony and titanium. Examples of such Lewis acids include aluminum chloride, aluminum bromide, boron tribromide, born trifluoride, zinc chloride, zinc iodide, ferrous chloride, stannous chloride, bismuth chloride, antimony pentachloride, titanium tetrachloride, and the like. Aluminum chloride is one particular example.

The reaction may be carried out in any organic solvent, which is inert under the reaction conditions. Suitable solvents include halogenated solvents such as 1,2-dichloroethane dichloromethane, and the like or hydrocarbons such as xylene, toluene, and the like. Toluene is one particular example. The reaction can be carried out at 30 to 80° C.

The compound of Formula V is hydrogenated to cleave the phenethyl group and obtain an intermediate of Formula II. The reaction is carried out in a protic solvent over a palladium/carbon catalyst. Suitable protic solvents include methanol, ethanol, isopropanol, water, and mixtures thereof. Methanol is a particular example. The reaction is preferably carried out at 40 to 60° C. and 4 to 5 atmosphere pressure.

Acid addition salts of the compounds of Formulas I, II, IV and V may be prepared by methods known in the art. The base is reacted with a calculated amount of acid in a water miscible solvent such as acetone, ethanol or methanol, with subsequent isolation of salt by concentration and cooling. Alternatively, the base is reacted with an excess of the acid in a water immiscible solvent such as ethyl acetate, with the salt separating out spontaneously.

Methods known in the art may be used with the process of this invention to enhance any aspect of the process. The product obtained may be further purified by any techniques known to a person skilled in the art for example, by filtration, crystallization, column-chromatography, preparative high pressure liquid chromatography, preparative thin layer chromatography, extractive washing in solution or a combination of these procedures.

Pharmaceutical Compositions

The compound of Formula I, the enantiomers thereof or their mixtures, and the pharmaceutically acceptable acid addition salts thereof may be formulated into ordinary dosage forms such as, for example, tablets, capsules, pills, solutions, etc. and in these cases, the medicaments can be prepared by conventional methods, including a therapeutically effective amount of a compound of Formula I, or its pharmaceutically acceptable salts, pharmaceutically acceptable solvates, as described herein, along with a pharmaceutically acceptable carrier, and optionally but desirably, pharmaceutically acceptable excipients. In addition to the common dosage forms set out about, the compound of the present invention may also be administered by controlled release means and/or delivery devices. These compositions can be employed for methods of producing $\alpha_1$-adrenergic antagonistic action in mammals.

Formulation of the pharmaceutical compositions may be carried out in conventional manner using one or more physiologically and/or pharmaceutically acceptable carriers or excipients. Thus, the compounds and their pharmaceutically acceptable salts and solvates may be formulated for administration by inhalation or insufflation (either through the mouth or the nose) or oral, buccal, parenteral, or rectal administration.

Preparations for parenteral administration of the pharmaceutical compositions described herein include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

For oral administration, the pharmaceutical compositions may take the form of, for example, tablets or capsules prepared by conventional means with pharmaceutically acceptable excipients such as binding agents (for example, pregelatinized maize starch, polyvinylpyrrolidone, or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspension, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

The compounds may also be formulated in rectal compositions such as suppositories or retention enemas, for example, containing conventional suppository bases such as cocoa butter or other glycerides.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

By "therapeutically effective amount" is meant the quantity of a compound or composition according to the invention necessary to prevent, cure or at least partially arrest the symptoms of the disorder and its complications. Amounts effective to achieve this goal will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, for example, in Gilman et al., eds., 1900, "Goodman and Gilman's: The Pharmaceutical Bases of Therapeutics," $8^{th}$ ed., Pergamon Press; and Remington's Pharmaceutical Sciences," 1990, $17^{th}$ ed., Mack Publishing Co., Easton, Pa., each of which is hereby incorporated by reference.

Methods of Treatment

The invention provides a method of producing α-adrenergic antagonistic action in a mammal, including the administration of a therapeutically effective amount of a compound having the structure of Formula I, or its pharmaceutically acceptable salts, pharmaceutically acceptable solvates, esters, enantiomers, diastereomers, N-oxides, polymorphs, prodrugs or metabolites, as described herein.

The methods include administering to a mammal a therapeutically effective amount of a compound having the structure of Formula I, or its pharmaceutically acceptable salts, or pharmaceutically acceptable solvates as described herein.

The compound of Formula I and the acid addition salts thereof provided by the present invention exhibit $\alpha_1$-adrenergic blocking action, and thus they can be utilized for various treatments such as for benign prostatic hyperplasia, lower urinary tract dysfunction, prostatic hypertrophy, erectile dysfunction, detrusor instability, high intraocular pressure, sympathetically mediated pain, migraine (Headache, 1997, 37, 107–108), and high cholesterol. The compound of Formula I and the acid addition salts thereof provided by the present invention may have better tolerability profile than tamsulosin as indicated by the differences in the affinity profile of compound of Formula I and tamsulosin for $\alpha_{1A}$, $\alpha_{1B}$, $5HT_{1A}$ and $D_3$ receptors and the per se hypotensive effect in anaesthetized normotensive rats.

The administration of pharmaceutical compositions can be by injection or by gradual infusion over time. The compositions can be administered intravenously, intraperitoneally, intramuscularly, subcutaneously, intracavity, or transdermally. Preferred methods for delivery of the compositions include orally, by encapsulation in microspheres, by aerosol delivery to the lungs, or transdermally by iontophoresis or transdermal electroporation. Other methods of administration will be known to those skilled in the art.

EXAMPLES

The invention will be further described in the following examples, which demonstrate general synthetic procedures for the preparation of the disclosed compounds, as well as tests of properties of the prepared compounds. The examples do not limit the scope of the invention described in the claims.

The $\alpha_1$-adrenoceptor antagonist tamsulosin has also been reported to have subnanomolar affinity for $5\text{-HT}_{1A}$ and D-3 receptors. The reported selectivity for affinity at $\alpha_{1A}$ adrenoceptor vs $5\text{-HT}_{1A}$ and D-3 receptors is 6 and 2 fold respectively (J. Med. Chem., 2000, 43, 2183–2195).

Central $5HT_{1A}$ agonism is known to result in hypotension via systemic vasodialation (Pharmacology, 1998, 56(1), 17–29; J. Hypertens., 1988,6(2), 565–68). $5HT_{1A}$ receptors have been demonstrated to be involved in reflex activation of parasympathetic pregangalionic neurons to heart, (Br. J. Pharmacol., 1998, 25,409–417) ciliary muscle, (J. Psychopharmacol., 1999, 13, 391–397) and bladder (J. Pharmacol. Exp. Ther., 1999, 290, 1258–1269). Similarly, $D_3$ receptors are also known to regulate cardiovascular and kidney function (Curr. Opin. Nephrol. Hypertens., 2002, 11(1), 87–92; Acta Physiol. Scand., 2000, 168(1), 219–23; J. Hypertens., 2002, 20 (S3), S55–8; Clin. Exp. Hypertens., 2001. 23(1–2), 15–24). Thus, $5HT_{1A}$ and $D_3$ receptors are involved in modulation of cardiovascular system, which is linked to the manifestation of the adverse effects of $\alpha_1$-adrenoceptor antagonists.

The affinities of compound of Formula I, its corresponding (S) isomer, the corresponding racemate and tamsulosin were determined for $\alpha_1$-adrenoreceptor subtypes. Also, the affinity of compound of Formula I, and tamsulosin for $5HT_{1A}$ and $D_3$ receptors was evaluated.

Test 1: Activity at $\alpha_1$-adrenoceptor Subtypes a) Radioligand-receptor Binding Assays (Human Recombinant Receptors)

The affinities of compound of Formula I, its corresponding (S)-isomer, the corresponding racemate and tamsulosin were determined for $\alpha_1$-adrenoreceptor subtypes in radioligand-receptor binding experiments conducted using human recombinant receptors.

Chinese hamster ovary (CHO) cells which had been stably transfected with human $\alpha_{1A}$, $\alpha_{1B}$, or $\alpha_{1D}$-adrenoceptors (Keffel et al., Biochem. Biophys. Res. Commun., 2000, 272, 906–11) were cultured in an atmosphere of 5% $CO_2$/95% air at 37° C. in F-12 HAM medium supplemented with 10% heat-inactivated fetal calf serum, 1 mM glutamine, 100 U/ml penicillin and 0.1 mg/ml streptomycin. Selection pressure was maintained by regular addition of geneticin to the culture medium.

Competitive radioligand binding to the cloned subtypes of $\alpha_{1A}$-adrenoceptors was performed using [$^3$H]prazosin as the radioligand as described by Michel et al, Br. J. Pharmacol., 98, 883–889 (1989) with minor modifications. Experiments were performed in binding buffer consisting of 50 mM Tris, 10 mM $MgCl_2$ and 0.5 mM EDTA at pH 7.5 in a total assay volume of 1000 μl. The protein content typically was 40–60 μg/assay. The mixtures were incubated at 25° C. for 45 minutes. Incubations were terminated by rapid vacuum filtration over GF/C filters followed by two washes of the filters each with 10 ml ice-cold incubation buffer. Nonspecific binding was defined as binding in the presence of 10 μM phentolamine.

The $IC_{50}$ & Kd were estimated by using the non-linear curve fitting program using G Pad Prism software. The value of inhibition constant Ki was calculated from competitive binding studies by using Cheng & Prusoff equation [Cheng & Prusoff, *Biochem. Pharmacol.*, 22, 3099–3108 (1973)], $Ki=IC_{50}/(1+L/Kd)$, where L is the concentration of [$^3$H]prazosin used in the particular experiment. $K_d$ of [$^3$H]prazosin was determined from saturation binding studies. The values were tabulated as mean±SEM of pKi values, where pKi is the −log of Ki value. The results are summarized in Table I.

TABLE I

Radioligand Receptor Binding Assays: Human Recombinant receptors

| | pKi | | |
|---|---|---|---|
| Compound | $\alpha_{1A}$ | $\alpha_{1B}$ | $\alpha_{1D}$ |
| Tamsulosin | 10.32 ± 0.10 | 9.16 ± 0.08 | 10.09 ± 0.12 |
| Formula I | 10.66 ± 0.09 | 9.49 ± 0.06 | 9.97 ± 0.27 |
| (S)-isomer | 8.65 ± 0.05 | 7.66 ± 0.16 | 8.10 ± 0.29 |
| Racemate | 10.08 ± 0.08 | 8.96 ± 0.05 | 9.67 ± 0.23 |

The compound of Formula I has 102 fold greater affinity for $\alpha_{1A}$-adrenoreceptor subtype than the corresponding (S)-isomer.

b) In-vitro Functional Studies

In order to study selectivity of action of compound of Formula I, and tamsulosin towards different $\alpha_1$-adrenoceptor subtypes, the ability of the compounds to antagonize $\alpha_1$-arenreceptor agonist-induced contractile response on aorta ($\alpha_{1D}$), prostate ($\alpha_{1A}$) and spleen ($\alpha_{1B}$) was studied. Aorta, prostate and spleen tissues were isolated from urethane anaesthetized (1.5 gm/kg) male wistar rats. Isolated tissues were mounted in organ bath containing Krebs Henseleit buffer of following compostion (mM): NaCl 118; KCl 4.7; $CaCl_2$ 2.5; $MgSO_4.7H_2O$ 1.2; $NaHCO_3$ 25; $KH_2PO_4$ 1.2; glucose 11.5. Buffer was maintained at 37° C. and aerated with a mixture of 95% $O_2$ and 5% $CO_2$. A resting tension of 2 g (aorta) or 1 g (spleen and prostate) was applied to tissues. Contractile response was monitored using a force displacement transducer and recorded on chart recorders. Tissues were allowed to equilibrate for 2 hours. At the end of equilibration period, concentration response curves to norepinephrine (aorta) and phenylepinephrine (spleen and prostate) were obtained in absence and presence of tested compound (at concentrations of 0.1, 1 and 10 mM). Antagonist affinities were calculated and expressed as $pK_B$ vales in Table II.

To compare the differences in $pK_B$ at the $\alpha_1$-arenrenoceptor subtypes one-way ANOVA followed by Dunett 't' test was applied. A $p<0.05$ was considered statistically significant.

TABLE II

In vitro functional studies: Potency for rat $\alpha_1$-adrenoceptor subtypes

| | $pK_B$ | | |
|---|---|---|---|
| | $\alpha_{1A}$ | $\alpha_{1B}$ | $\alpha_{1D}$ |
| Tamsulosin | 10.51 ± 0.17 | 9.56 ± 0.15* | 10.54 ± 0.15 |
| Formula I | 10.79 ± 0.24 | 9.30 ± 0.20* | 11.23 ± 0.14 |

*p < 0.05 (as compared to $pK_B$ at prostate tissue).

In the functional assays the compound of Formula I has significantly greater $\alpha_{1A}$ versus $\alpha_{1B}$ selectivity (31 fold) as compared to tamsulosin, which exhibits 9 fold selectivity.

Test 2: Activity at $5-HT_{1A}$ Receptors a) Radioligand-receptor Binding Assays (Human Recombinant Receptors)

Receptor binding assays were performed using human recombinant $5HT_{1A}$ receptors. The affinities of compound of Formula I, and tamsulosin for $5HT_{1A}$ were evaluated in the radioligand binding assays conducted according to Martin et al., *Neuropharmacol.*, 1993, 33, 261 with minor modifications, using [$^3$H]8-OH-DPAT as the radioligand. Non-specific binding was defined by 10 μM Metergoline. The results are displayed in Table III.

TABLE III

Radioligand Receptor Binding Assays: $5HT_{1A}$ Human recombinant receptors

| | PKi |
|---|---|
| Tamsulosin | 9.10 |
| Formula I | 8.01 |

The compound of Formula I has 12.6 fold lower affinity for $5HT_{1A}$ receptors than tamsulosin. Also, the compound of Formula I has 27 fold greater $\alpha_{1A}$ versus $5HT_{1A}$ selectivity as compared to tamsulosin (Tables I and III).

Test 3: Activity at $D_3$ Receptors a) Radioligand-receptor Binding Assays (Human Recombinant Receptors)

Receptor binding assays were performed using human recombinant $D_3$ receptors. The affinities of compound of Formula I, and tamsulosin were evaluated as described by Sokoloff et al., *Nature*, 1999, 347, 146 with minor modifications, using [$^3$H]Spiperone as the radioligand. Non-specific binding was defined by 25 μM S(−)Sulpiride. Results are displayed in Table IV.

TABLE IV

Radioligand Receptor Binding Assays: $D_3$ Human recombinant receptors

| | PKi |
|---|---|
| Tamsulosin | 9.55 |
| Formula I | 8.75 |

The compound of Formula I has 6 fold lower affinity for $D_3$ receptors than tamsulosin. Also, the compound of Formula I has 14 fold greater $\alpha_{1A}$ versus $D_3$ selectivity as compared to tamsulosin (Table I and IV).

Test 4: Hypotensive Effect in Rats

Male normotensive rats were anaesthetised with urethane (1.2 g/kg, i.p.). Carotid artery and femoral vein were cannulated for recording blood pressure and administration of test compounds respectively. Trachea was cannulated to maintain the airway patency. Rats were divided into two groups of 10 rats each. Group I received compound of Formula I, and Group II received Tamsulosin. Compounds were administered cumulatively at dose level of 0.01, 0.03, 0.1, 0.3, 1 & 10 μg/kg and effects on blood pressure and heart rate were monitored. Each subsequent dose in cumulative dose range was administered after previous response had stabilized.

Blood pressure and heart rate were recorded before and after drug treatment on a Grass polygraph using a Statham pressure transducer and tachograph. Effect on blood pressure was expressed as percentage change from the basal level. $ED_{20}$ was calculated by fitting the cumulative dose response data in non-linear regression analysis and the value was taken from the curve. Effect on heart rate was expressed as change in beats/min.

To compare the difference amongst the dose groups one-way ANOVA followed by Dunett 't' test was applied. A p of <0.05 was considered statistically significant. The results are displayed in Table V.

TABLE V

| Hypertensive effect in anaesthetised normotensive rats | |
|---|---|
| | $ED_{20}$ (ng/kg) |
| Tamsulosin | 300 |
| Formula I | 520 |

$ED_{20}$: Effective dose to produce a fall in blood pressure by 20%.

Figure 1B:
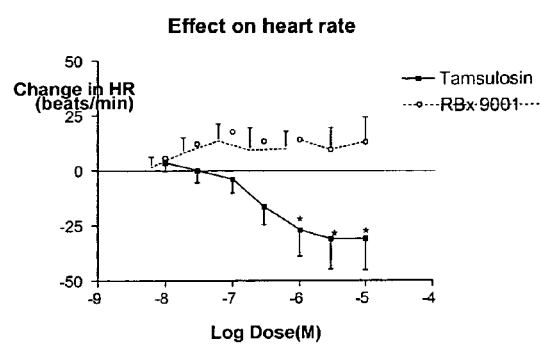
FIG. 1b is a graph of the effect of log of the concentration of tamsulosin and of the compound of Formula I on the heart rate of normotensive rats, as expressed in change of heart rate in beats per minute.

The compound of Formula I and tamsulosin resulted in dose dependent fall in blood pressure. The per se hypotensive effect was significantly greater for tamsulosin ($ED_{20}$ 300 ng/kg) as compared to the compound of Formula I ($ED_{20}$ 520 ng/kg). In tamsulosin treated animals fall in the blood pressure was accompanied by decrease in the heart rate, whereas in animals treated with the compound of Formula I this decrease in blood pressure is accompanied by increase in heart rate, as shown in FIGS. 1a & 1b.

Example 1

Preparation of (3-sulfonamido-4-methoxyphenyl)-2-propanone 4-methoxyphenyl acetone was added slowly to chlorosulphonic acid (20 ml) at −5 to +5° C. with stirring. The temperature was raised to 15° C. and the reaction mixture stirred for 4 hours at the same temperature. The reaction mixture was then added slowly to a mixture of ethyl acetate (100 ml) and water (200 ml) at 0° C. The temperature was raised to 20° C., the organic layer was separated and washed with brine. The organic layer was concentrated under reduced pressure to dryness and toluene (10 ml) was added to the residue. The solution obtained was stirred, toluene was recovered completely under vacuum and the residue was dissolved in THF at 40° C. The solution was cooled to 10° C. and NH3 gas purged slowly to attain pH~8.8–9.8 at 8–12° C. The temperature was raised to 20–25° C. and stirred for 15 hours maintaining pH~9.0. The solid obtained was filtered, washed with THF, water and then methanol and dried under vacuum at 60° C. to get 4.2 g of the title compound.

Example 2

Preparation of R,R-2-Methoxy-5-[2-(1-phenylethylamino)-propyl]benzenesulfonamide, hydrochloride (Formula IV)

(3-sulfonamido-4-methoxyphenyl)-2-propanone obtained from Example 1 was added to methanol (300 ml) and activated Raney Ni (1.5 g) in a hydrogenation flask. R(+)-1-phenyl ethylamine (1 g) was added and hydrogen gas was applied at a pressure of 3.5 bar. Temperature was raised to 50° C. and pressure raised to 5.5. bar. The reaction mixture was cooled to room temperature and Raney Ni filtered through hyflo bed. The filtrate was concentrate under reduced pressure at 50° C. and toluene (10 ml) was added. The resultant solution was concentrated at 50–60° C. under reduced pressure to recover toluene completely and get a thick oil (3 g approx.) of the title compound.

Example 3

Preparation of R,R-2-hydroxy-5-[2-(1-phenylethylamino)propyl]benzenesulfonamide (Formula V)

R,R-2-Methoxy-5-[2-(1-phenylethylamino)-propyl]benzenesulfonamide, hydrochloride (Formula IV, 12 g, 0.03 moles) and anhydrous aluminium chloride (24.0 g, 0.18 mmoles) were added to toluene (120 ml) at room temperature. Temperature of the reaction mass was raised to 80° C. and the mixture was stirred at this temperature for around two hours. Reaction mixture was then cooled to room temperature and poured on crushed ice. The water/toluene mixture was decanted to get a sticky mass. The product was dissolved in water (100 ml) under warming. Aqueous ammonia was added to increase pH to about 9 to 10. The basic solution was extracted with ethyl acetate and the solvent was removed under reduced pressure. Crude product so obtained was recrystallized from ethyl acetate to get the title compound (7.0 g).

The mass spectrum showed a peak at (MH$^+$): 335. The $^1$H-NMR spectrum showed (DMSO-d$_6$; δ, ppm); 0.77 (d, 3H), 1.22 (d, 3H) 2.27–2.35 (m, 1H), 2.44–2.51 (m, 1H), 2.76–2.82 (m, 1H), 3.88–3.93 (m, 1H), 6.85 (d, 1H), 7.04–7.38 (m, 7H). The infrared spectrum showed (KBr, cm$^{-1}$); 3378, 3280, 2972, 1687, 1604, 1461, 1302.

Example 4

Preparation of R-5-(2-aminopropyl)-2-hydroxybenzenesulfonamide (Formula II)

The compound from Example 3 (6.0 g, 0.018 moles) and palladium/carbon catalyst (3.0 gm, 5%) were added to methanol (200 ml) and stirred under hydrogen pressure of 5.0 kg at 50° C. for around 20 hours. The reaction mixture was cooled and the catalyst filtered off. The filtrate was concentrated under reduced pressure to obtain the title product as a solid (3.35 g).

The mass spectrum (MH$^+$) showed: 231. The $^1$H-NMR spectrum showed (DMSO-d$_6$; δ, ppm); 1.02 (d, 3H), 2.34–2.50 (m, 1H), 2.66–2.73 (m, 1H), 3.07–3.16 (m, 1H), 6.83 (d, 1H), 7.11 (d, 1H), 7.38 (s, 1H). The infrared spectrum (KBr, cm$^{-1}$) showed: 3172, 1602, 1469, 1312.

Example 5

Preparation of R,R-2-hydroxy-5-[2-(1-phenylethylamino)propyl]benzenesulfonamide, hydrochloride (Formula V, hydrochloride)

R,R-2-hydroxy-5-[2-(1-phenylethylamino)-propyl]benzenesulfonamide, (10 g, 0.03 moles) was dissolved in methanol (50 ml) by addition of methanolic hydrogen chloride slowly to get a pH of about 3. Methanol was removed under reduced pressure and acetone (60 ml) was added to the residue. The solvent (50 ml) was removed under reduced pressure and acetone (200 ml) was further added to the residue with stirring. The solid was separated out. The suspension was then cooled to 0° C. and stirred for one hour. The solid was filtered, washed with acetone and dried to get the title compound (9.0 g) as a white solid.

The melting point was: 237.7° C. The optical rotation was $[\alpha]_D$: +31.71°(c=1.0, methanol). The mass spectrum (MH$^+$) showed: 335. The $^1$H-NMR spectrum (DMSO-d$_6$; δ, ppm) showed: 1.11 (d, 3H), 1.65 (d, 3H) 2.50–2.61 (m, 1H), 2.89 (bs, 1H), 4.60–4.63 (m, 1H), 6.9–7.1 (m, 4H), 7.32 (s, 1H), 7.4–7.75 (m, 5H), 9.32 (bs, 1H), 10.0 (bs, 1H), 10.74 (s, 1H). The infrared spectrum (KBr, cm$^{-1}$)showed: 3275, 3064, 2973, 2810, 1612, 1587, 1500, 1455, 1426.

Example 6

Preparation of R-5-(2-aminopropyl)-2-hydroxybenzenesulfonamide, hydrochloride (Formula II, hydrochloride)

The compound from Example 5 (5.0 g, 0.0135 moles) and palladium/carbon catalyst (2.50 gm, 5%) were added to methanol (50 ml) and stirred under hydrogen pressure of 5.5 kg at 50° C. for around 2 hours. The reaction mixture was cooled and the catalyst filtered off. The filtrate was concentrated under reduced pressure. Ethyl acetate (50 ml) was added to the residue and 50% of the solvent was distilled off. The resulting suspension was cooled to 0 to 5° C. The solid was filtered, washed with ethyl acetate and dried to obtain the title product (3.35 g).

The melting point was 267.1° C. (decomposition). The optical rotation was $[\alpha]_D$: −6.51° (c=1.0, methanol). The mass spectrum (MH$^+$) showed: 231. The $^1$H-NMR spectrum (DMSO-d$_6$; δ, ppm) showed: 1.11 (d, 3H), 2.58–2.66 (m, 1H), 2.94–3.0 (m, 1H), 3.25–3.4 (m, 1H), 6.92 (s, 1H), 7.02 (d, 1H), 7.27 (dd, 1H), 7.50 (d, 1H), 8.12 (bs, 3H), 10.73 (s, 1H). The infrared spectrum (KBr, cm$^{-1}$) showed: 3527, 3351, 3039, 1608, 1502, 1427, 1322.

Example 7

Preparation of R (−)-5-[2-[[2-(2-ethoxyphenoxy) ethyl]amino]propyl]-2-hydroxybenzenesulfonamide, hydrochloride (Formula I, hydrochloride)

The compound from Example 6 (2.0 g, 0.0087 moles) and 2-(2-ethoxyphenoxy) acetaldehyde (1.8 g, 0.01 moles) were added to methanol (100 ml) at room temperature followed by sodium cyanoborohydride (0.63 g, 0.1 moles). The reaction mixture was then stirred for around 20 hours. Methanol was then removed under reduced pressure. Water (10 ml) and acetic acid (0.001 g) were added to the residue and the product was extracted from the resulting solution with ethyl acetate. The organic layer was concentrated under reduced pressure and the residue was dissolved in methanol. Concentrated hydrochloric acid was added to the methanolic solution till a pH of about 3.0. The hydrochloride salt was precipitated by adding ethyl acetate. It was filtered and dried to obtain the title compound (0.6 g).

The mass spectrum (MH$^+$) showed: 395. The $^1$H-NMR spectrum (DMSO-d$_6$; δ, ppm) showed: 1.15 (d, 3H), 1.26 (t, 3H), 2.62 (t, 1H), 3.22–3.27 (m,1H), 3.43–3.50 (m, 3H), 4.02 (q, 2H), 4.29 (brt, 2H), 6.88–7.08 (m, 7H), 7.28 (d, 1H), 7.54 (s, 1H), 9.20 (brs, 2H), 10.75 (brs, 1H). The infrared spectrum (KBr, cm$^{-1}$) showed: 3198, 2978, 2486, 1592, 1505, 1424, 1339.

Example 8

Preparation of R (−)-5-[2-[[2-(2-ethoxyphenoxy) ethyl]amino]propyl]-2-hydroxybenzenesulfonamide (Formula I)

The compound from Example 7, (2.0 g, 0.0075 mole) was taken in methanol (10 ml) and 2-(2-ethoxyphenoxy)acetaldehyde (2.35 g. 0.013 mole) was added, and the mixture was cooled to 10° C. Sodium cyanoborohydride (0.47 g, 0.0075 moles) was added slowly. Reaction mixture was then stirred at room temperature for about 20 hours. Hydrochloric acid (dilute) was added slowly to the reaction mixture to get a pH~3.0 and stirred the solution for 30 min. Thereafter methanol was removed under reduced pressure. A mixture of ethyl acetate, diisopropyl ether water and was added and stirred at 50–55° C. for 15 minutes. Aqueous layer was separated, cooled to 10° C. and basified with liq. NH$_3$ to pH~9.0. The suspension was stirred for 1 hour at 10° C. The solid obtained was filtered, washed with water and dried to obtain 1.86 gm of the title product (crude). The crude product was refluxed in methanol and then cooled to 0.5° C. Filtration and washing with methanol yielded the title product (1.61 g) in pure form.

The melting point was 159.5° C. The optical rotation was $[\alpha]_D$: −3.59° (c=1.0, 0.1N methanolic HCl). Optical purity (by HPLC): 99.93%. The mass spectrum showed (MH$^+$): 395. The $^1$HNMR spectrum (DMSO-d6, δ, ppm) showed: 0.92 (d, 3H), 1.29 (t, 3H), 2.37–2.44 (dd, 1H), 2.69–2.75 (dd, 1H), 2.81–2.91 (m, 3H), 3.83–4.0 (m, 5H), 6.88–6.96 (m, 5H), 7.21 (d, 1H), 7.46 (s, 1H). The infrared spectrum (KBr, cm$^-$) showed: 3194, 2924, 1589, 1506, 1463, 1412, 1321.

Example 9

Preparation of R (−)-5-[2-[[2-(2-ethoxyphenoxy) ethyl]amino]propyl]-2-hydroxybenzenesulfonamide, hydrochloride (Formula I, hydrochloride)

The compound from Example 8 was dissolved in methanol. Concentrated hydrochloric acid was added to the methanolic solution till a pH of about 3.0. The hydrochloride salt was precipitated by adding ethyl acetate. It was filtered and dried to obtain the title compound (1.3 g).

The melting point was 153.7° C. The optical rotation was $[\alpha]_D$: −3.21° (c=1.0, methanol). Optical purity (by HPLC): 99.77%.

While the present invention has been described in terms of its specific embodiments, certain modifications and equivalents will be apparent to those skilled in the art and are intended to be included within the scope of the present invention.

We claim:

1. A method for the preparation of the compound of Formula I,

Formula I

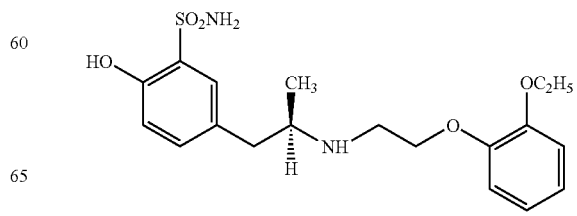

and pharmaceutically acceptable acid addition salts thereof, which comprises condensing the chiral primary amine of Formula II, or a salt thereof, with an aldehyde of Formula III in the presence of sodium cyanoborohydride followed by isolation of the enantiomer of Formula I as the free base, or a pharmaceutically acceptable acid addition salt thereof,

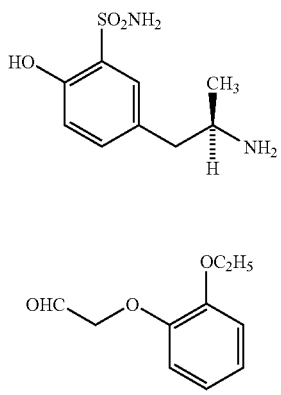
Formula II

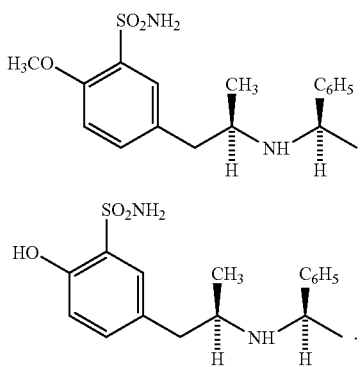
Formula IV

Formula V

Formula III wherein the chiral primary amine of formula II is prepared by reacting the chiral phenethylamine compound of Formula IV, or a salt thereof, with a Lewis acid and hydrogenating the obtained 2-hydroxybenzenesulfonamide compound of Formula V or a salt thereof, to get the intermediate of Formula II, 2. The method of claim 1, further comprising converting the intermediate of Formula II to a salt form.

3. The method of claim 1, wherein the Lewis acid is a halide of aluminum, boron, zinc, iron, tin, bismuth, antimony or titanium.

4. The method of claim 3, wherein the Lewis acid is aluminum chloride.

* * * * *